United States Patent [19]

Van Der Puy et al.

[11] Patent Number: 4,705,896

[45] Date of Patent: Nov. 10, 1987

[54] NOVEL EXTRACTANTS FOR THE RECOVERY OF PALLADIUM

[75] Inventors: Michael Van Der Puy; David S. Soriano, both of Cheektowaga; Jeffrey H. Dimmit, Williamsville, all of N.Y.

[73] Assignee: Allied Corporation, Morris Township, Morris County, N.J.

[21] Appl. No.: 624,068

[22] Filed: Jun. 25, 1984

[51] Int. Cl.$^4$ ............................................. C07C 131/00
[52] U.S. Cl. ................................... 564/265; 564/266; 423/DIG. 14; 423/24; 423/658.5
[58] Field of Search ............................... 564/265, 266; 423/DIG. 14, 24, 658.5

[56] References Cited

U.S. PATENT DOCUMENTS

| | | | |
|---|---|---|---|
| 3,428,449 | 2/1969 | Swanson | 564/266 |
| 3,437,431 | 4/1969 | Platz et al. | 23/50 |
| 3,922,330 | 11/1975 | Pittie et al. | 423/22 |
| 3,967,956 | 7/1976 | Payne | 423/22 |
| 4,052,194 | 10/1977 | Wilcox | 564/265 |
| 4,133,834 | 1/1979 | Pickens | 564/258 |
| 4,158,015 | 6/1979 | Paul | 564/265 |
| 4,331,634 | 5/1982 | Shanton et al. | 423/22 |

FOREIGN PATENT DOCUMENTS

| | | | |
|---|---|---|---|
| 0012158 | 6/1980 | European Pat. Off. | 564/265 |
| 2518631 | 4/1975 | Fed. Rep. of Germany. | |
| 2013644 | 8/1979 | United Kingdom. | |
| 2104516 | 3/1983 | United Kingdom. | |

OTHER PUBLICATIONS

Juhasz, Attila et al., *Chemical Abstracts*, vol. 93, (1980), #150,641u.
Chemical Abstracts Registry Handbook, 1981 Supplement, pp. 1394RJ and 1435RJ.
Buu-Hoi, et al., J. Org. Chem., 1955, 20, p. 606.
G. N. Vyas, et al., Org. Synthesis Coll., 1963, 4, p. 836.
Lachman, Org. Synthesis Cell., 1943, 2, p. 70.
McOmie, et al., Org. Synthesis Coll., 1973, 5, p. 412.
Laskorin, et al., "The Effect Fo Structure 2-Hydroxyphenonoximes on the Formation of the Copper Compleses", Proc. Int. Solvent Extr. Conf., 1974, 2, pp. 1775–1790.

*Primary Examiner*—Paul J. Killos
*Attorney, Agent, or Firm*—Jay P. Friedenson

[57] ABSTRACT

Novel ortho alkoxy substituted phenyl oxime compounds which are useful for selectively separating and recovering palladium from aqueous compositions and mixtures containing palladium and other metals.

12 Claims, No Drawings

NOVEL EXTRACTANTS FOR THE RECOVERY OF PALLADIUM

BACKGROUND OF THE INVENTION

1. Field of Art

This invention relates to a novel compound for the recovery and purification of palladium. More particularly, this invention relates to novel ortho alkoxy substituted phenyl oxime compounds which are capable of selectively separating and recovering palladium from aqueous compositions and mixtures containing palladium and other metal ions such as aluminum, nickel, iron, copper, other platinum family metals, rhodium, ruthenium, platinum and the like.

2. Prior Art

The recovery and purification of platinum group metals, such as palladium and platinum, is an important commercial process. For example, such processes are useful in the recovery of palladium from solutions obtained in the recovery of mineral deposits of the platinum metals, which solutions commonly contain in addition to palladium, ruthenium, rhodium, iridium and platinum, and small quantities of base metals such as iron, and nickel. Such processes are also useful in the recovery of palladium from spent catalyst materials, such as automobile catalytic converters.

Several extraction methods have been developed for recovery of palladium metal values. Solvent extraction processes for the recovery of metal values have certain well recognized advantages over other recovery methods, and such solvent extraction processes are increasing in number and types of applications. Fundamental to a successful solvent extraction process for the recovery palladium is the identification of a water immiscible composition (combination of compounds which will selectively bind to palladium and a suitable solvent) which will selectively extract palladium from an aqueous solution containing palladium, other platinum group metals and other metals. A further requirement for a successful palladium metal recovery by the solvent extraction techniques is an extracting composition having the property such that palladium metal values extracted by the extracting solvent can be recovered from same using another suitable aqueous phase.

Illustrative of such prior art solvent extraction processes are those described in U.S. Pat. No. 3,967,956 and in United Kingdom Pat. No. 20,136,443. In the processes of these patents, palladium is recovered from a mixture of palladium and other platinum group metals through use of an extracting composition containing ortho hydroxyoxime compounds, such as alkyl substituted ortho-hydroxyphenyl oxime compounds. The extracted palladium metal is removed from the extracting solvent by contacting same with a strongly acidic aqueous solution. This method is generally a useful procedure for recovering certain metals from the extracting solvent because the recovery procedure is pH dependent. With ortho-hydroxy phenyl oxime compounds, the extraction process is dependent on the ionizable nature of the phenolic hydrogen, and in the $Cu^{+2}$ system is generally believed to follow the following equilibrium in which "LH" is the un-ionized oxime:

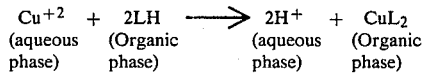

Presumably, the $Pd^{+2}$ system would operate in a similar manner when being extracted by ortho-hydroxy phenyl oxime compounds, In which case, palladium metal values are extracted into the organic water immiscible extracting solvent as the neutral species $PdL_2$, while LH ionizes so that the acidity of the aqueous phase increases. Recovery by treatment with strong acid is effective because by shifting the equilibrium, the oxime is protonated releasing the palladium as $Pd^{+2}$ which migrates into the polar aqueous phase.

SUMMARY OF THE INVENTION

In accordance with this invention there is provided a small class of ortho alkoxy substituted phenyloxime compounds which are useful in the extraction of palladium from aqueous solution of palladium and other metals. The compounds of this invention are of the formula:

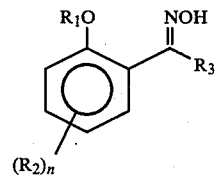

wherein:

n is an integer of from 1 to 4;

$R_1$ is alkyl, cycloalklyl, or aralkyl;

$R_2$ is nitro, halogen, hydrogen, or substituted or unsubstituted cycloalkyl, alkoxy, alkyl, aryloxy, aryl, aralkyl or alkaryl wherein permissible substituents are those which are inert under the use conditions of the compound when extracting and isolating palladium metal values; and $R_3$ is alkyl, aryl, cycloalkyl, alkaryl or aralkyl either unsubstituted or substituted with one or more of the above-referenced permissible substitutents, with the proviso that $R_2$ and $R_3$ together contain a total of 7 or more carbon atoms.

The novel extractants of this invention obviate many of the deficiencies of the hydroxy substituted phenyl oxime compounds heretofore used for extraction of palladium metal. For example, certain of the novel compounds of this invention can selectively extract palladium from aqueous solutions of palladium and other metals including copper. Moreover, other of the novel compounds of this invention are able to selectively extract palladium without the need for ion exchange columns.

DESCRIPTION OF THE PREFERRED EMBODIMENTS

The compounds of this invention are those of the formula:

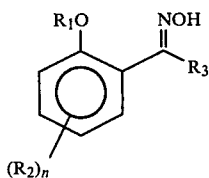

wherein n, $R_1$, $R_2$ and $R_3$ are as described above.

The following compounds are illustrative of compounds within the purview of the generic formula set forth above, all of which can be conveniently prepared by simply selecting appropriate reactants for use in the procedures described herein below:

(2-Methoxy-5-methyl)phenyl nonyl ketoxime
(2-Methoxy-5-methyl)phenyl pentadecyl ketoxime
2-Methoxy-5-nonyl benzophenone oxime
2-Methoxy-5-heptadecylbenzaldoxime
2-Methoxy-5-nonyl-4'-methyl benzophenone oxime
[2-Methoxy-5-(α,α-dimethylbenzyl)] phenyl hexyl ketoxime
(2-Ethoxy)phenyl pentadecyl ketoxime
2-Methoxy-4-phenyl benzophenone oxime
(2-Methoxy-4-chloro-5-methyl)phenyl pentadecyl ketoxime
2-Methoxy-3,5-dinonyl benzophenone oxime
2-Methoxy-3,5-dinonyl acetophenone oxime
2-Methoxy-5-nonyl-4'-chloro benzophenone oxime
2-Methoxy-5-(t-butyl)-3'-hexyl benzophenone oxime
2-Methoxy-4'-methyl benzophenone oxime
(2-Methoxy-5-nitro)phenyl 2'-napthyl ketoxime
2-Ethoxy-5-nonyl benzaldoxime
(2-Methoxy-4-methyl)phenyl 4'-fluorophenyl ketoxime
(2-Methoxy-4-methyl)phenyl benzyl ketoxime
2-Methoxy-4'-phenyl benzophenone oxime
2,4-Dimethoxy-4'-methyl benzophenone oxime
(2-Ethoxy-4-phenoxy)phenyl propyl ketoxime Illustrative of suitable $R_1$ groups are alkyl such as methyl, ethyl, propyl, isopropyl, isobutyl, butyl, octyl, nonyl, pentyl, hexyl, heptyl and the like; aralkyl such as benzyl, and the like; and cycloalkyl such as cyclopentyl, cyclohexyl and the like.

Exemplary of useful $R_3$ substituents are hydrogen, and the above described illustrative $R_1$ substituents. Illustrative of useful $R_2$ substituents are methoxy, nitro, phenoxy, chloro, fluoro, hydrogen and the above-referenced $R_1$ substituents. These $R_2$ and $R_3$ groups may be unsubstituted or substituted with one or more substituents which are inert to the extraction and stripping process. Illustrative of such permissible substituents are alkyl, halogen, aryl, cycloalkyl, nitro, alkoxy, aryloxy and the like.

Preferred are compounds of the above-referenced generic formula in which n is 1 or 2, and $R_1$, $R_2$ and $R_3$ are as described above with the proviso that $R_2$ is substituted at the 4th and/or 5th position on the phenyl ring.

Particularly preferred are compounds of the above referenced generic formula in which:

n is 1 or 2;

$R_1$ is straight chain alkyl having from 1 to about 6 carbon atoms; and $R_2$ and $R_3$ are the same or different and are unsubstituted alkyl, aralkyl, aryl or alkaryl with the proviso that the $R_2$ substituent is substituted at the 4th and-/or 5th positions on the phenyl ring, and with the further proviso that $R_2$ and $R_3$ contain a total of from about 16 to about 30 carbon atoms. Amongst these particularly preferred, compounds most preferred are compounds of the aforementioned generic formula in which:

n is 1;

$R_1$ is straight chain alkyl having from 1 to about 3 carbon atoms;

$R_2$ is straight chain alkyl having from 1 to about 12 carbon atoms, with the proviso that the $R_2$ group is substituted at the 4th position on the phenyl ring; and $R_3$ is straight chain alkyl having from about 15 to about 25 carbon atoms and phenyl.

Especially efficacious compounds are those of the above-referenced formula in which $R_1$ is methyl, $R_2$ is straight chain alkyl having from 1 to about 9 carbon atoms; and $R_3$ is phenyl or straight chain alkyl having from about 12 to about 25 carbon atoms. Illustrative of these especially efficacious compounds are 2-methoxy-5-nonyl benzophenone oxime and (2-methoxy-5-methyl)phenyl pentadecyl ketoxime.

The compounds of this invention can be conveniently prepared by a variety of methods. One preferred method for preparing the compounds of this invention is illustrated in the following Reaction Scheme A.

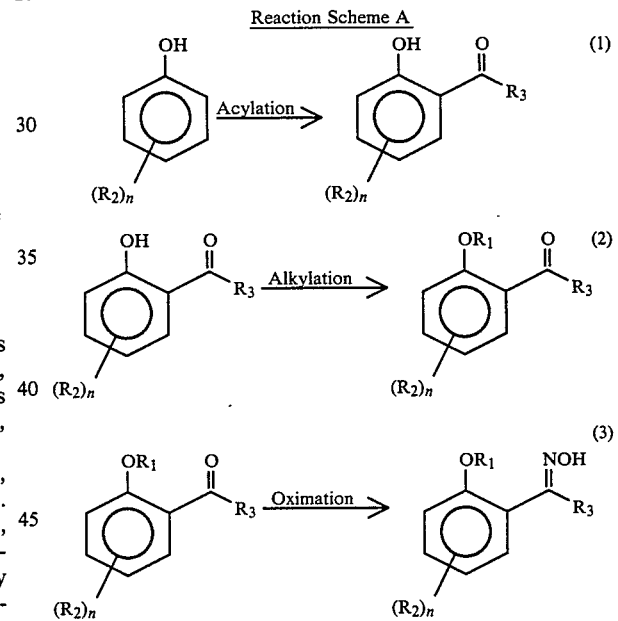

wherein n, $R_1$, $R_2$ and $R_3$ are as described above.

In the first step of the process, a substituted phenol is acylated to give the corresponding phenol containing an ortho substituted acyl group, the acylation reaction can be carried out using conventional acylation techniques. The acylation of substituted phenols may be accomplished by several techniques. One method which utilizes the condensation of a phenol with a benzotrichloride catalyzed by aluminum chloride is described by M. S. Newman and A. G. Pinkus (*J. Org. Chem.*, 1954, 19, 985–1002). Another method which can be employed in the acylation step is the condensation of a phenol with a carboxylic acid using boron trifluoride as a catalyst, as described by N. P. Buu-Hoi and J. Seailles (*J. Org. Chem.*, 1955, 20, 606). The acylation reaction may be conducted without a solvent, as the reaction mixtures are generally fluid at typical reaction temperatures of from 75° to about 150° C. Alternatively, aprotic inert solvents such as trichloroethylene or carbon tetrachloride may be used as a solvent.

Generally, when boron trifluoride is used as a catalyst, gaseous boron trifluoride is bubbled subsurface into the reaction mixture at atmospheric pressure. Other equivalent procedures, such as the use of an atuoclave, are apparent to those skilled in the art. Good yields of arylated product are obtained when the phenol or substituted phenol is present in excess (1.2-1.6 molar equivalents) in order to insure monoacylation. Preferably, a para-substituted phenol is also used to insure ortho-acylation. Para-acylation yields material which does not selectively form a complex with divalent palladium and which generally is less stable under the use conditions.

Separation of the product (acylated phenol) from the starting phenol will usually depend on the substituents on the phenol and the acyl group, and on other factors known to those of skill in the art and must therefore be determined on a case by case basis through use of known scientific principles. For example, when p-cresol is used as the substituted phenol, and the acyl group contains a long hydrocarbon chain, the product can be separated from the starting material by pouring the reaction mixture into methanol. p-Cresol is soluble in methanol whereas the desired product is insoluble.

The temperature required for the acylation depends to a large degree on the catalyst used and other factors known to those of skill in the art. For example, when boron trifluoride is used as the catalyst, the reaction rate increases with increasing temperature until a temperature is reached such that gaseous boron trifluoride boils out of the reaction flask when the reaction is conducted at atmospheric pressure. Thus, a temperature of from about 120° to about 130° C. seems to be the optimum for carrying out the acylations under these conditions.

In the second step of the process, the phenolic group is alkylated with an appropriate alkylating agent such as an alkyl halide or dimethyl sulfate. A number of techniques are possible for the alkylation of the phenolic group. For some phenols, procedures typical of alkyl aryl ether syntheses may be employed. For example, an alkylating agent such as ethanolic NaOH and an alkylating agent such as dimethylsulfate, or potassium carbonate in acetone containing an alkyl iodide can be employed. Such procedures are exemplified in the literature by G. N. Vyas and N. M. Shah (*Org. Synthesis Coll,* Vol. 4, 836 (1963).

Other alkylation methods which involves phasetransfer catalyzed alkylation of the phenol can be employed. In this procedure, an aqueous phase containing suitable base such as NaOH and a phase transfer catalyst such as tetra-n-butylammonium bromide is contacted with a water-immiscible organic solvent such as methylene chloride containing the dissolved phenol and an alkylating agent such as methyl iodide.

In the phase transfer reaction there is considerable flexibility in the choice of base used, the phase transfer catalyst, the organic solvent and the alkylating agent. The base can be an alkali metal hydroxide or carbonate, i.e., bases which are alkaline enough to ionize the acylated phenol. The base is used in at least a stoichiometric amount relative to the phenol. The phase transfer catalyst is usually a quaternary alkyl ammonium halide or hydroxide, and can be used in less than stoichiometric amounts (e.g., 0.01 to 0.1 equivalents). The important feature of the phase transfer catalysts is that, with hydroxide as the counterion, it has substantial solubility in the organic solvent. Alternatively, crown ethers can be employed as the phase transfer catalyst, but are generally more expensive.

The organic solvent should be immiscible with water and should readily dissolve the acylated phenol. Suitable solvents are the chlorinated methanes and ethanes and aromatic hydrocarbons solvents such as toluene and benzene.

Alkylation reactions under phase transfer conditions are commonly performed at a temperature of from about 0° to about 40° C. The upper temperature is limited by the boiling point of the aqueous or organic phase, whichever is lower.

Finally, in the third step of the process the carbonyl portion of the compound is oximated with a conventional oximation agent, such as hydroxylamine. The oximation of the carbonyl compound can be carried out by treating the compound with hydroxylamine in an alcohol solvent such as ethanol or methanol at reflux for 2 to 3 hours. A typical oximation procedure from the literature is that described by A. Lachman, *Org. Synthesis Coll.* Vol. 2, 70 (1943).

For the oximation of the aryl alkyl ketones, preferably a slight excess (1.05-1.15 equivalents) of an hydroxylamine salt (the hydrochloride or sulfate) is neutralized with sodium hydroxide, or sodium or potassium carbonate in aqueous solution or in a water-alcohol co-solvent. If a co-solvent is used which has relatively low water content, the neutralization by-product, e.g., sodium chloride, will not be soluble and can be filtered, if desired. The ketone, dissolved in alcohol is then added. The reaction mixture is refluxed 1 to 2 hours during which time additional alcohol can be added to maintain homogeneity. On cooling the reaction mixture, the product oxime will often separate as a solid or an oil. Otherwise, the volatile alcohol solvent can be removed and the residue washed with water providing the solid or liquid oxime.

Alternatively, the compounds of this invention can be prepared by a variation of the procedure of Reaction Scheme A, which variation is depicted in Reaction Scheme B.

Reaction Scheme B

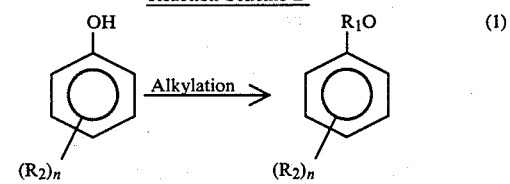
(1)

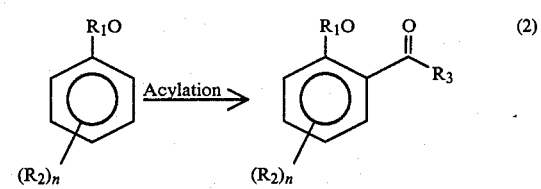
(2)

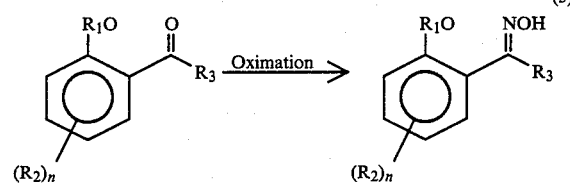
(3)

In Reaction Scheme B, steps one and two of Reaction Scheme A are reversed; that is in step 1 of Scheme B, an appropriate phenol compound is alkylated or arylated as in step 2 of Scheme A, to provide a substituted alkoxy benzene and in step 2 of Scheme B the substituted benzene is acylated as in step a of Scheme A to provide the intermediate ketone which can be oximated in accordance with step 3 of Reaction Scheme A.

In practice, Scheme B is less desirable than Scheme A in certain instances. This is because in the presence of acylation catalysts such as boron trifluoride and boron tribromide dealkylation of the alkoxybenzene or aryloxy benzene to give phenol can occur during the acylation procedure. See, for example, J. F. W. McOmie and D. E. West, *Org. Synthesis Coll.*, Vol. 5, 412 (1973). Thus, a second alkylation procedure would be required.

The phenols and carboxylic acids or their equivalents employed as reactants in the reactions of Reaction Schemes A and B are known compounds which can be obtained from commercial sources or prepared in accordance with conventional preparation methods known to those of skill in the art. Thus, procedures for preparing these reactants will not be described herein in great detail.

Reaction Schemes A and B are carried out over a period of time sufficient to produce the desired compound in adequate yield. Reaction times are influenced to a significant degree by the reaction temperature; the concentration and choice of reactants; the choice and concentration of reaction solvent and by other factors known to those skilled in the art. In general, reaction times can vary from about a few minutes to 24 hours or longer. In most instances, when employing preferred reaction conditions, reaction times will be found to vary from about 1 hour to about 3 hours.

The process of Reaction Schemes A and B can be conducted in a batch, semicontinous or continuous fashion. The reactants and reagents may be initially introduced into the reaction zone batchwise or they may be continuously or intermittently introduced in such zone during the course of the process. Means to introduce and/or adjust the quantity of reactants introduced, either intermittently or continuously into the reaction zone during the course of the reaction can be conveniently utilized in the process especially to maintain the desired molar ratio of the reaction solvent, reactants and reagents. The reaction can be conducted in a single reaction zone or in a plurality of reaction zones, in series or in parallel or it may be conducted intermittently or continuously in an elongated tubular zone or series of such zones. The materials of construction employed should be inert to the reactants during the reaction and the fabrication of the equipment should be able to withstand the reaction temperatures and pressure.

The reaction zone can be fitted with one or more internal and/or external heat exchanger(s) in order to control undue temperature fluctuations, or to prevent any possible "runaway" reaction temperatures. In preferred embodiments of the process, agitation means to vary the degree of mixing the reactions mixture can be employed. Mixing by vibration, shaking, stirring, rotation, oscillation, ultrasonic vibration or the like are all illustrative of the type of agitation means contemplated. Such means are available and well known to those skilled in the art.

The compounds of this invention are useful for the selective extraction of palladium from aqueous solutions containing palladium and other metals such as copper, platinum, rhodium, manganese, iridium, zinc, ruthenium, iron, nickel, cobalt, lead and aluminum. The method of using the novel compounds of this invention in such application is described in more detail in our copending U.S. patent application Ser. No. 626,956 for "Novel Composition and Method for the Recovery of Palladium", filed July 2, 1984. Briefly stated, in the process of our co-pending patent application, the recovery of palladium values is accomplished as follows. The pH of an aqueous solution of palladium and other metals is adjusted preferably to a pH of from about 0 to about 5. The aqueous acidic solution is contacted (with good mixing) with the novel oxime compound of this invention neat or dissolved in an appropriate water immiscible organic solvent in which the oxime has a solubility of 2% by weight or more, and one whose boiling point is greater than the temperature of the stripping and extraction operation. Appropriate solvents include aliphatic and aromatic hydrocarbons such as benzene, toluene, xylene, kerosenes, fuel oils and the like, as well as halogenated solvents. The concentration of oxime in the solution is greater than about 2 weight percent based on the total weight of the solvent, and is preferably from about 5 to about 25 weight percent. After the contact or extraction period, all or a portion of the palladium will be extracted into the organic phase. The two immiscible phases are separated using standard techniques. The organic phase containing the palladium metal values can be stripped of the metal value using an aqueous solution of ammonia having a normality of from 1 to about 11. The extraction and stripping temperature is usually in the range of from about room temperature to about 100° C. The organic phase containing the solvent and the free oxime can then be recycled to the extraction step, as described above. Recovery of the palladium can then be accomplished by the addition of HCl to the ammonia solution to precipitate $Pd(NH_3)_2Cl_2$ as an insoluble salt. Pure palladium can be formed from this salt by procedures well-known in the refining of platinum group metals.

The following specific examples are presented to more particularly illustrate the invention.

EXAMPLE I

1. Preparation of (2-Methoxy-5-methyl)phenyl Pentadecyl Ketoxime

A mixture of 54 g (0.5 mol) p-cresol and 64.5 g (0.25 mol) palmitic acid was heated to 85°–90° C. for 3 hours, during which time a steady stream of $BF_3$ was added. The mixture was brought to 130° C. for an additional hour. After cooling, the reaction mixture was poured into ice water, with stirring. The product was collected by filtration, and then treated with 200 mL of boiling methanol to dissolve entrained p-cresol. The slurry was filtered, and the solid washed with cold methanol and dried to give (2-hydroxy-5-methyl)phenyl pentadecyl ketone in 84% yield; mp 54°–55° C.

IR (Nujol): 1640 cm$^{-1}$(C=O).

NMR (CDCl$_3$): δ6.8–7.5 (3H), 2.95 (t, 2H), 2.2 (s, 3H), 1.2 (31H).

The above hydroxyphenyl ketone (50 g, 0.15 mol) and 42.6 g (0.30 mol) iodomethane were dissolved in 100 mL methylene chloride. This solution was stirred rapidly at 40° C. with a solution of 42 g (0.75 mol) potassium hydroxide and 4.7 g (0.015 mol) tetra-n-butylammonium bromide in 100 mL water. The reaction time was 5 hours. After cooling the reaction mixture, the phases were separated. The aqueous layer was extracted with 50 mL methylene chloride which was then added to the original methylene chloride layer. The combined organic layers were dried over anhydrous magnesium sulfate and concentrated under vacuum to an oil. The oil was taken up in petroleum ether and filtered to remove residual ammonium salt. The filtrate was again concentrated under vacuum to provide a light yellow oil, identified as (2-methoxy-5-methyl)phenyl pentadecyl ketone. The yield was 91%.

IR (thin film): 1660 cm$^{-1}$ (C=O).

NMR (CDCl$_3$): δ6.8–7.1 (3H), 3.8 (s, 3H, OC$\underline{H}_3$), 2.75 (t, 2H), 2.2 (s, 3H, ArC$\underline{H}_3$), 1.2 (31H).

The above (2-methoxy-5-methyl)phenyl pentadecyl ketone was transformed into the corresponding ketoxime as follows. A solution of 1.94 g (0.028 mol) hydroxylamine hydrochloride in 50 mL methanol was neutralized, under a nitrogen atmosphere, by the addition of 1.57 g potassium hydroxide. After stirring 1 hour, the slurry was filtered to remove potassium chloride and 7.8 g (0.022 mol) of (2-methoxy-5-methyl) phenyl pentadecyl ketone was added to the filtrate. The resulting mixture was refluxed overnight. Methanol was removed under vacuum and the residue taken up in 100 mL methylene chloride which was then washed with 100 mL water. The methylene chloride layer was dried, and the solvent removed under vacuum to give 8.25 g (97% yield) of (2-methoxy-5-methyl)phenyl pentadecyl ketoxime, mp 51°–52° C. after recrystallization from ethanol-water. The infrared spectrum indicated the absence of the C=O bond of the starting material.

NMR (CDCl$_3$): δ6.7–7.2 (m, 3H), 3.77 (s, 3H, OC$\underline{H}_3$), 2.75 (t, 2H), 2.3 (s, 3H, ArC$\underline{H}_3$), 1.2 (31H, aliphatic).

2. Extraction of Palladium

A solution of 5 weight percent (2-methoxy-5-methyl) phenyl pentadecyl ketoxime in kerosene (Kermac 627 a kerosene manufactured and sold by Kerr-McGee) was prepared. A second solution was prepared by dissolving K$_2$PdCl$_4$ in dilute hydrochloric acid (pH=1). The concentration of palladium was 1028 ppm as determined by atomic absorption spectroscopy. The aqueous solution of K$_2$PdCl$_4$ was shaken with an equal volume of the first solution containing the oxime for 12 hours at room temperature. The two phases were separated and the aqueous phase analyzed for palladium content. The palladium concentration in the aqueous phase was found to be only 0.27 ppm, indicating greater than 99.9% extraction of the palladium present in the original aqueous solution.

EXAMPLE II

1. Preparation of 2-methoxy-5-nonyl benzophenone oxime

A sample of 2-hydroxy-5-nonyl benzophenone (25 g, 0.077 mol) was dissolved in 100 mL methylene chloride. To this solution was added a solution of 20 g (0.5 mol) sodium hydroxide in 100 mL deionized water, followed by the addition of 22 g (0.154 mol) iodomethane and 2.5 g (0.006 mol) tetra-n-butylammonium bromide. The entire mixture was agitated with vigorous mechanical stirring for 1.5 hours at 45° C. The reaction mixture was allowed to cool, and the layers separated. The aqueous phase was extracted with 50 mL methylene chloride. The combined organic layers were dried over anhydrous magnesium sulfate and concentrated under vacuum. The residual oil was taken up in petroleum ether, washed with water, dried over magnesium sulfate and again concentrated under vacuum to provide 22 g (85% yield) of 2-methoxy-5-nonyl benzophenone.

IR(film): 1660 cm$^{-1}$ (C=O). NMR (CDCl$_3$): δ6.8–7.7 (m, 8H), 3.7 (s, 3H, OC$\underline{H}_3$), 0.4–1.8 (m, 19H).

To 50 mL methanol (at 0° C. under nitrogen) was added 4.6 g (0.067 mol) hydroxylamine hydrochloride. Potassium hydroxide 3.75 g (0.067 mol) was then added and the mixture stirred 0.5 hours. Filtration of the resultant slurry was performed quickly, and the filtrate returned to the reaction flask. To the methanol solution of hydroxylamine was then added 2-methoxy-5-nonyl benzophenone, 22 g (0.065 mol), and the resulting mixture refluxed under nitrogen for 12 hours. The reaction mixture was cooled, and concentrated under vacuum to an oil. The oil was taken up in 75 mL methylene chloride and washed with an equal volume of water. The organic layer was then separated, dried over anhydrous magnesium sulfate and the volatiles removed under vacuum to give an oil (15 g, 65% yield) identified as 2-methoxy-5-nonyl benzophenone oxime. IR indicated the loss of C=O stretch at 1660 cm$^{-1}$.

NMR (CDCl$_3$): 6.8–7.7 (m, 8H), 3.75 (s, 3H, OCH$_3$; a singlet at δ3.65 also appeared, which corresponds to the second geometrical isomer, the ratio of isomers being about 85:15), 0.4–1.8 (m, 19H).

2. Extraction of Palladium

A 5% by weight solution of 2-methoxy-5-nonyl benzophenone oxime in kerosene (Kermac 627) was prepared. This solution was agitated for 12 hours with an equal volume of an aqueous solution containing 930 ppm divalent palladium at a pH of 5. After the extraction period, analysis of the aqueous phase indicated only 1 ppm palladium present. This represents the extraction of about 99.9% of the palladium present in the original aqueous phase.

EXAMPLE III

1. Preparation of 2-isopropoxy-5-nonyl benzophenone Oxime

2-Isopropoxy-5-nonyl benzophenone was prepared as follows. To 25 g of 2-hydroxy-5-nonyl benzophenone in 100 mL CH$_2$Cl$_2$ was added 20 g NaOH in 100 mL water, followed by the addition of 48 g isopropyl bromide and 2.5 g tetra-n-butyl-ammonium bromide. The entire mixture was stirred vigorously at 40° C. for 3 days. The reaction mixture was worked up as described for the preparation of 2-methoxy-5-nonyl benzophenone (Example II) to give 16 g of yellow oil (57% yield), identified as the desired product.

IR(film): 1660 cm$^{-1}$ (C=O).

NMR (CDCl$_3$); δ6.8–7.7 (m, 8H), 4.2 (m, 1H, (CH$_3$)$_2$C$\underline{H}$13 ), 0.2–1.5 (m, 25H).

To 150 mL methanol (at 0° C. and under nitrogen) was added 2.4 g hydroxylamine hydrochloride. Sodium hydroxide (2.0 g) was then added to the above solution and stirring continued for 1 hour. The slurry was quickly filtered to remove NaCl, and the filtrate was returned to the reaction flask. The above ketone, 12.0 g, was then added and the mixture stirred at room temperature overnight. The next day, an additional 5 g hydroxylamine hydrochloride was added, and the mixture refluxed for 12 hour more. The mixture was then cooled, the methanol removed under vacuum, and the residue taken up in 75 mL CH$_2$Cl$_2$. The methylene chloride solution was washed with 75 mL water, separated, dried (MgSO$_4$) and the volatiles removed under vacuum to provide 12.6 g (100% yield) of the desired 2-isopropoxy-5-nonyl benzophenone oxime (oil). IR(film) indicated complete loss of the C=O bond.

NMR (CDCl$_3$): δ6.8–7.4 (m, 8H), 4.4 (m, 1H), 0.4–1.8 (m, 25H).

2. Extraction of Palladium

An aqueous solution containing 200 ppm Pd(II) at pH 4 was stirred with an equal volume of a 5 weight-/volume percent solution of 2-isopropoxy-5-nonyl benzophenone oxime in kerosene at room temperature for 10 minutes. The two layers were then separated and the aqueous layer analyzed for palladium content. The analysis indicated 110 ppm Pd(II) in the aqueous phase or 45% uptake of the palladium by the oxime extractant.

EXAMPLE IV

1. Preparation of 2-n-pentoxy-5-nonyl benzophenone Oxime

A solution of 2-hydroxy-5-nonyl benzophenone, 15 g, in 100 mL methylene chloride was mixed with a solution of 9.25 g NaOH in 100 mL water. To this mixture was added 6.9 g n-pentyl bromide and 1.48 g tetra-n-butylv ammonium bromide. The whole mixture was then vigorously agitated overnight at 40° C. After cooling to room temperature with 50 mL CH$_2$Cl$_2$. The combined methylene chloride layers were concentrated to an oil, which was taken up in 100 mL petroleum ether and washed with 100 mL water. Finally, the organic layer was dried over anhydrous magnesium sulfate and the volatiles removed under vacuum to give 15 g (82% yield) of 2-n-pentoxy-5-nonyl benzophenone.

NMR (CDCl$_3$): δ6.8–7.4 (m, 8H), 3.8 (t, 2H), 0.2–1.7 (m, 28H).

The above ketone was oximated as described in Examples 2 and 3 using 2.1 g hydroxylamine hydrochloride neutralized with 1.7 g potassium hydroxide in 125 mL methanol. The methanolic hydroxylamine solution was refluxed overnight with 6 g of the above ketone. Work-up provided 6.0 g (98% yield) of an oil identified as 2-pentoxy-5-nonyl benzophenone oxime. IR (film) indicated complete absence of the C=O bond, and the presence of an OH stretch at about 3300 cm$^{-1}$.

NMR (CDCl$_3$): δ6.8–7.3 (m, 8H), 3.8 (t, 2H), 0.8–1.6 (m, 28H).

2. Extraction of Palladium

A solution of 0.5 g of the above oxime was dissolved in 10 mL kerosene. (Kermac 627) This was stirred for 10 minutes with 10 mL of an aqueous solution containing 334 ppm Pd(II) at pH 4. After the 10 minute extraction period, the phases were separated and the aqueous phase analyzed for palladium content. The results indicated 38 ppm palladium in the aqueous phase or a 89% uptake of the palladium by the oxime extractant.

EXAMPLE V

1. Preparation of 2-methoxy-5-nonylacetophenone

A solution of p-nonylphenol, 35 g, in 125 mL methylene chloride was mixed with a solution of 44.5 g KOH in 125 mL water. To this mixture was added 45 g iodomethane and 5.0 g tetra-n-butylammonium bromide. The whole mixture was vigorously stirred at 40° C. for one hour. After cooling to room temperature, the phases were separated and the aqueous phase extracted with 50 mL methylene chloride. The combined methylene chloride layers were concentrated to an oil which was taken up in 200 mL of petroleum ether and filtered to remove the residual phase transfer catalyst. Finally, the petroleum ether was removed under vacuum to give 31.1 g (84%) of p-nonylanisole.

NMR (CDCl$_3$): δ6.6–7.3 (m, 4H), 3.75 (s, 3H), 0.5–1.8 (m, 19H).

A mixture of the above anisole (31 g) and glacial acetic acid (15 g) was heated to 70° C. for five hours, during which time a steady stream of BF$_3$ was added. After cooling the reaction mixture, it was dissolved in 200 mL methylene chloride and washed with 200 mL water. The organic layer was dried (MgSO$_4$) and the solvent was removed under vacuum to give 32.5 g of a red oil identified as a mixture of p-nonyl 2-methoxy-5-nonylacetophenone (major product) and 2-hydroxy-5-nonylacetophenone. To ensure complete conversion to the methoxyketone, the product mixture was re-alkylated by the phase transfer reaction described above. Work-up of the reaction mixture yielded 31.5 g (88%) of 2-methoxy-5-nonylacetophenone.

NMR(CDCl$_3$): δ7.95 (d, 1H), 6.9 (apparent d 2H), 3.8 (s, 3H), 2.5 (s, 3H), 0.5–1.8 (m, 19H); IR (thin film) 1675 cm$^{-1}$(C=O).

The above methoxyketone was oximated as described in Example II, III, and IV using 10 g of hydroxylamine hydrochloride neutralized with 8.1 g potassium hydroxide in 250 mL methanol. The methanolic hydroxylamine solution was stirred overnight with 31.5 g of the ketone. Work-up yielded 28.5 g of an oil identified as 2-methoxy-5-nonylacetophenone oxime.

NMR (CDCl$_3$): δ9.5 (b, 1H), 7.55 (d, 1H), 6.86 (apparent d, 2H), 3.8 (s, 3H), 2.25 (s, 3H), 0.5–1.9 (m, 19H).

IR (thin film) indicated complete absence of the C=O bond.

2. Extraction of Palladium

A solution of 5 grams of the above oxime in 95 grams of kerosene was made. Ten mL of this solution was contacted with 10 mL of an aqueous solution containing 1900 ppm Pd(II) at pH 3. After a 12 hour extraction period, the phases were separated and the aqueous phase analyzed for palladium content. The results indicated 4.7 ppm palladium in the aqueous phase or 99.7% uptake of the palladium by the oxime extractant.

EXAMPLE VI

1. Preparation of (2-methoxy-5-methyl)phenyl Nonyl Ketoxime

Decanoic acid (43 g) and p-cresol (54 g) were combined and heated to 80°–90° C. for 4–5 hours, while BF$_3$ was slowly bubbled into the solution. The solution was cooled and poured into ice-water. The oil was extracted with benzene and the benzene solution distilled to remove benzene and unreacted p-cresol. The distillation pot residue was washed with aqueous potassium carbonate to provide crude (2-hydroxy-5-methyl)phenyl nonyl ketone.

NMR (CDCl$_3$): δ7.6 (s, 1H, OH), 6.8–7.4 (3H, aromatic), 2.95 (t, 2H), 2.35 (s, 3H), 0.8–1.9 (m, 17H); IR (film): 1640 cm$^{-1}$.

A solution of the above ketone (17.5 g) in 100 mL methylene chloride was mixed with a solution of 4.0 g NaOH in 100 mL water. To this mixture was added 9.9 g iodo methane and 1.2 g benzyl tri-n-butylammonium bromide. The whole mixture was stirred vigorously at room temperature overnight. After twelve hours an additional 23 g iodomethane was added and the reaction mixture heated to 40° C. with continued stirring for an additional four hours. After cooling to room temperature, the phases were separated and the aqueous phase extracted with 75 mL methylene chloride. The combined methylene chloride layers were dried over anhydrous magnesium sulfate and the solvent removed under vacuum to yield 13.6 g (74%) of (2-methoxy-5-methyl)phenyl nonyl ketone.

NMR (CDCl$_3$): δ6.7–7.5 (m, 3H), 3.8 (s, 3H), 2.9 (T, 2H), 2.25 (s, 3H), 0.5–1.9 (m, 19H).

IR (thin film): 1670 cm$^{-1}$ (carbonyl).

The ketone was oximated as described earlier in Examples 2 and 3 using 3.5 g of hydroxylamine hydroxychloride neutralized with 2.0 g sodium hydroxide in 50 mL methanol. The methanolic hydroxylamine solution was stirred overnight with 13.0 g of the ketone. The work-up yielded 13.9 g of a yellow oil that was vacuum distilled to yield 8.7 g of a compound identified as (2-methoxy-5-methyl)phenyl nonyl ketoxime (bp 154°–185° C./1 mm Hg).

NMR (CDCl$_3$): δ6.8–7.2 (m, 3H), 3.8 (s, 3H), 2.7 (t, 2H), 2.2 (s, 3H), 0.5–1.8 (m, 17H).

2. Extraction of Palladium

A solution of 2.5 g of the above oxime in 45 g kerosene was made. Ten mL of this solution was contacted with 10 mL of an aqueous solution containing 371 ppm Pd(II) at pH = 1. After a twelve hour extraction period, the phases were separated and the aqueous phase analyzed for palladium content. The results indicated 0.6 ppm palladium in the aqueous phase or 99.8% uptake of palladium by the oxime extractant.

What is claimed is:

1. A compound of the formula:

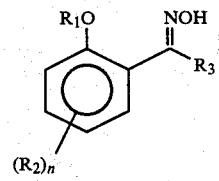

wherein:

n is an integer of from 1 to 4;

R$_1$ is alkyl from 1 to 6 carbon atoms, cycloalkyl, or aralkyl;

R$_2$ is nitro, halogen, hydrogen or substituted or unsubstituted alkyl, alkoxy, aryloxy, cycloalkyl, aryl, aralkyl or alkaryl wherein permissible substituents are those which are inert under the use conditions of the compounds when extracting and isolating palladium metal values; and R$_3$ is alkyl having from 12 to 25 carbon atoms, either unsubstituted or substituted with one or more of the aforementioned permissible subsituents.

2. A compound according to claim 1 wherein n is 1 or 2.

3. A compound according to claim 2 wherein n is 1.

4. A compound according to claim 1 wherein R$_1$ is straight chain alkyl having from 1 to about 3 carbon atoms.

5. A compound according to claim 4 wherein R$_1$ is methyl.

6. A compound according to claim 1 wherein R$_2$ and R$_3$ are different, wherein R$_2$ is unsubstituted alkyl, aralkyl, aryl or alkaryl with the proviso that said R$_2$ substituent is substituted at the meta and/or para positions relative to the oxime function, and wherein R$_3$ is unsubstituted alkyl, with the further proviso that R$_2$ and R$_3$ together contain a total of from about 12 to about 30 carbon atoms.

7. A compound according to claim 6 wherein R$_2$ is substituted at the meta position relative to the oximono function.

8. A compound according to claim 7 wherein R$_2$ is straight chain alkyl having from 1 to about 12 casrbon atoms.

9. A compound according to claim 6 wherein R$_3$ is straight chain alkyl.

10. A compound according to claim 1 selected from the group consisting of (2-methoxy-5-methyl) phenyl pentadecyl ketoxime, 2-methoxy-5-nonyl benzophenone oxime, 2- isoporpoxy-5-nonyl benzophenone oxime, and 2-(nopentoxy)-5-nonyl benzophenone oxime, 11. (2-Methoxy-5-methyl)phenyl pentadecyl ketoxime.

12. 2-Methoxy-5-nonyl benzophenone oxime.

* * * * *

UNITED STATES PATENT AND TRADEMARK OFFICE
CERTIFICATE OF CORRECTION

PATENT NO. : 4,705,896
DATED : November 10, 1987
INVENTOR(S) : Van Der Puy et al.

Page 1 of 5

It is certified that error appears in the above-identified patent and that said Letters Patent are hereby corrected as shown below:

In the Specification

Column 8, line 59
    delete "IR (Nujol)"; substitute therefor -- <u>IR (Nujol)</u> --.

Column 8, line 59
    delete "(C=O)."; substitute therefor -- (C=O); --.

Column 8, line 60
    delete "NMR (CDCl$_3$)"; substitute therefor -- <u>NMR (CDCl$_3$)</u> --.

Column 9, line 11
    delete "IR (thin film)"; substitute therefor -- <u>IR (thin film)</u> --.

Column 9, line 11
    delete "(C=O)."; substitute therefor -- (C=O); --.

Column 9, line 12
    delete "NMR (CDCl$_3$)"; substitute therefor -- <u>NMR (CDCl$_3$)</u> --.

Column 9, line 12
    delete "OCH$_3$"; substitute therefor -- OC<u>H</u>$_3$ --.

Column 9, line 13
    delete "ArCH$_3$"; substitute therefor -- ArC<u>H</u>$_3$ --.

UNITED STATES PATENT AND TRADEMARK OFFICE
CERTIFICATE OF CORRECTION

PATENT NO. : 4,705,896
DATED : November 10, 1987
INVENTOR(S) : Van Der Puy et al.

It is certified that error appears in the above-identified patent and that said Letters Patent are hereby corrected as shown below:

Column 9, line 32
    delete "NMR (CDCl$_3$)"; substitute therefor -- <u>NMR (CDCl$_3$)</u> --.

Column 9, line 32
    delete "OC<u>H</u>$_3$"; substitute therefor -- OC<u>H</u>$_3$ --.

Column 9, line 33
    delete "ArC<u>H</u>$_3$"; substitute therefor -- ArC<u>H</u>$_3$ --.

Column 10, line 3
    delete "IR (film)"; substitute therefor -- <u>IR (film)</u> --.

Column 10, line 3
    delete "(C=O):"; substitute therefor -- (C=O); --.

Column 10, line 3
    delete "NMR (CDCl$_3$)"; substitute therefor -- <u>NMR (CDCl$_3$)</u> --.

Column 10, line 4
    delete "OC<u>H</u>$_3$"; substitute therefor -- OC<u>H</u>$_3$ --.

Column 10, line 22
    delete "NMR (CDCl$_3$)"; substitute therefor -- <u>NMR (CDCl$_3$)</u> --.

Column 10, line 52
    delete "IR (film)"; substitute therefor -- <u>IR (film)</u> --.

UNITED STATES PATENT AND TRADEMARK OFFICE
CERTIFICATE OF CORRECTION

PATENT NO. : 4,705,896
DATED : November 10, 1987
INVENTOR(S) : Van Der Puy et al.

It is certified that error appears in the above-identified patent and that said Letters Patent are hereby corrected as shown below:

Column 10, line 52
    delete "(C=O)."; substitute therefor -- (C=O); --.

Column 10, line 53
    delete "NMR (CDCl$_3$)"; substitute therefor -- NMR (CDCl$_3$) --.

Column 10, line 54
    delete "CH13"; substitute therefor -- CH- --.

Column 11, line 4
    delete "NMR (CDCl$_3$)"; substitute therefor -- NMR (CDCl$_3$) --.

Column 11, line 33
    delete "NMR (CDCl$_3$)"; substitute therefor -- NMR (CDCl$_3$) --.

Column 11, line 44
    delete "NMR (CDCl$_3$)"; substitute therefor -- NMR (CDCl$_3$) --.

Column 12, line 4
    delete "NMR (CDCl$_3$)"; substitute therefor -- NMR (CDCl$_3$) --.

Column 12, line 21
    delete "NMR (CDCl$_3$)"; substitute therefor -- NMR (CDCl$_3$) --.

UNITED STATES PATENT AND TRADEMARK OFFICE
CERTIFICATE OF CORRECTION

PATENT NO. : 4,705,896

DATED : November 10, 1987

INVENTOR(S) : Van Der Puy et al.

It is certified that error appears in the above-identified patent and that said Letters Patent are hereby corrected as shown below:

Column 12, line 31
    delete "NMR ($CDCl_3$)"; substitute therefor -- NMR ($CDCl_3$) --.

Column 12, line 59
    delete "NMR ($CDCl_3$)"; substitute therefor -- NMR ($CDCl_3$) --.

Column 12, line 61
    delete "IR (film)"; substitute therefor -- IR (film) --.

Column 13, line 9
    delete "NMR ($CDCl_3$)"; substitute therefor -- NMR ($CDCl_3$) --.

Column 13, line 11
    delete "IR (thin film)"; substitute therefor -- IR (thin film) --.

Column 13, line 22
    delete "NMR ($CDCl_3$)"; substitute therefor -- NMR ($CDCl_3$) --.

In the Claims

Claim 1, Column 14, line 10
    delete "12"; substitute therefor -- 15 --.

Claim 6, Column 14, line 27
    delete "12"; substitute therefor -- 16 --.

UNITED STATES PATENT AND TRADEMARK OFFICE
CERTIFICATE OF CORRECTION

PATENT NO. : 4,705,896

DATED : November 10, 1987

INVENTOR(S) : Van Der Puy et al.

It is certified that error appears in the above-identified patent and that said Letters Patent is hereby corrected as shown below:

Claim 8, Column 14, line 33
   delete "casrbon"; substitute therefor -- carbon --.

Claim 10, Column 14, line 38
   delete ") phenyl"; substitute therefor -- )phenyl --.

Claim 10, Column 14, line 40
   delete "2- isoporpoxy"; substitute therefor
-- 2-isopropoxy --.

Claim 10, Column 14, line 41
   delete "nopentoxy"; substitute therefor -- n-pentoxy --.

Signed and Sealed this

Sixth Day of September, 1988

Attest:

DONALD J. QUIGG

Attesting Officer     Commissioner of Patents and Trademarks